(12) United States Patent
Petersen et al.

(10) Patent No.: US 7,270,744 B2
(45) Date of Patent: Sep. 18, 2007

(54) AUTOMATED LOW-VOLUME TANGENTIAL FLOW FILTRATION PROCESS DEVELOPMENT DEVICE

(75) Inventors: Cristopher Petersen, Amherst, NH (US); Bradley Wolk, Montara, CA (US)

(73) Assignee: Millipore Corporation, Billerica, MA (US)

( * ) Notice: Subject to any disclaimer, the term of this patent is extended or adjusted under 35 U.S.C. 154(b) by 581 days.

(21) Appl. No.: 10/928,483

(22) Filed: Aug. 27, 2004

(65) Prior Publication Data

US 2005/0023194 A1    Feb. 3, 2005

Related U.S. Application Data

(63) Continuation-in-part of application No. 10/264,948, filed on Oct. 4, 2002, now abandoned.

(60) Provisional application No. 60/327,911, filed on Oct. 9, 2001.

(51) Int. Cl.
*B01D 61/22*    (2006.01)

(52) U.S. Cl. .................. 210/85; 210/195.2; 702/2

(58) Field of Classification Search ............ 210/195.2, 210/85, 134, 143, 321.65; 702/1
See application file for complete search history.

(56) References Cited

U.S. PATENT DOCUMENTS

| | | | |
|---|---|---|---|
| 3,567,031 A | 3/1971 | Loeffler | 210/321 |
| 3,893,920 A | 7/1975 | Hubbard et al. | 210/321 |
| 4,743,372 A | 5/1988 | Kumagai et al. | 210/195.2 |
| 5,270,159 A | 12/1993 | Ichikawa et al. | 430/569 |
| 5,693,229 A | 12/1997 | Hartmann | 210/650 |
| 5,855,792 A | 1/1999 | Adams et al. | 210/696 |
| 5,947,689 A | 9/1999 | Schick | 417/19 |
| 6,296,770 B1 | 10/2001 | Wilcox et al. | 210/651 |
| 6,592,708 B2 | 7/2003 | Vanell | 156/345.1 |
| 6,656,359 B1 | 12/2003 | Osuda et al. | 210/636 |

(Continued)

FOREIGN PATENT DOCUMENTS

DE    19740327 A1    9/1997

(Continued)

OTHER PUBLICATIONS

"*Amicon Inc. U.S. Catalog*", Amicon Publication No. 323, p. 53 (1994).

(Continued)

*Primary Examiner*—Terry K. Cecil
(74) *Attorney, Agent, or Firm*—Nields & Lemack

(57) ABSTRACT

An automated process development device providing flexibility and accuracy for the investigative development of tangential flow filtration (tff) processes and used for evaluating the process parameters of a laboratory scale tff process with an eye towards developing a commercial scale process. The device—operable to a recirculation volume of less than 20 milliliters—includes: a reservoir having a distinct mixing zone; a tff module; conduits defining a fluid process stream through which a liquid sample is recirculated; pumps for driving and valves for regulating the flow of the liquid sample through the stream; sensors for acquiring data about the sample as it flows through the stream; and an electronic data processing network capable of receiving, transmitting, processing, and recording data associated with the operation of the pumps, valves, and sensors, the recorded data being sufficiently comprehensive to determine the conduct of the tangential flow filtration process at a substantially larger scale.

7 Claims, 11 Drawing Sheets

U.S. PATENT DOCUMENTS

2001/0037966 A1    11/2001    Petersen et al. ......... 210/195.2

FOREIGN PATENT DOCUMENTS

| EP | 0995483 A1 | 10/1998 |
| JP | 2000-15298 A | 1/2000 |
| RU | 2170606 C1 | 10/1999 |

OTHER PUBLICATIONS

"*Filtron U.S. Catalog*", Filtron Technology Corporation Publication, pp. 48-51 (May 1992).

"*Labscale TFF System*", http://www.millipore.com/biopharm/products.nsf/docs/4ENNJ8 (downloaded Aug. 9, 2001).

"*Filter Products for the Pharmaceutical Industry: MINIM*", http://domino.pall.com (downloaded Aug. 3, 2001).

"*Tangential Flow Filtration Devices and Systems*", http://www.millipore.com/bipharm/products.nsf/docs/4B3LXP (downloaded Sep. 4, 2001).

"*Tangential Flow Filtration*", http://www/wedgewoodtech.com/appl_flow_filtration.htm (downloaded Oct. 2, 2001).

R. van Reis et al., "*Protein Purification using High Performance Tangential Flow Filtration with Charged Membranes*", http://www.che.utoledo.edu/nams98/scripts (downloaded Oct. 2, 2001).

"*Filtration Solutions for R&D: Process Development*", http://www.pall.com/applicat/ bio_pharm/r_and_d/why_filt_important.asp (downloaded Sep. 4, 2001).

PCT International Search Report for PCT/US02/31900 (Forms PCT/ISA/210 and 220)(mailed Jan. 21, 2003).

AUTOMATED LOW-VOLUME TANGENTIAL FLOW FILTRATION PROCESS DEVELOPMENT DEVICE

The present application is a continuation-in-part of U.S. patent application Ser. No. 10/264,948, filed Oct. 4, 2002, now abandoned, which claims the benefit of U.S. Prov. Pat. App. Ser. No. 60/327,911, filed Oct. 9, 2001.

FIELD

In general, the present invention is directed to a tangential flow filtration system, and more particularly, to an automated tangential flow filtration system for separation process analysis and development.

BACKGROUND

The filtration of a liquid sample by a membrane for purposes of purification (e.g., by removal of particulate or molecular contaminants) or concentration (e.g., for laboratory analysis) is a well developed art. Toward such ends, the flow of the liquid sample relative to the membrane's surface can in many instances be meaningfully characterized as either essentially parallel (i.e., tangential flow) or essentially normal (i.e., normal flow).

In a tangential flow filtration system, a large fraction of the liquid sample flows continuously, over time, in a direction essentially parallel to the membrane surface, as opposed to a much smaller portion which flows through the membrane. Because of the sweeping, cleansing nature of such flow—which discourages premature clogging, fouling, and concentration polarization—tangential flow filtration systems can often attain higher fluxes and higher throughputs than corresponding normal flow membrane filter systems. Because of these and other advantages, TFF systems are often pivotally employed for filtration in industrial drug manufacturing processes.

In the development of an industrial-scale drug filtration process there is often a need to timely investigate and qualify certain important parameters of the process, for example, its membrane characteristics, the flow path configuration and dynamics, the process' sequence of steps, and the allowable range of operating conditions. In drug development, timeliness is particularly important because a final "approved" manufacturing process often rests heavily upon its early foundations, and the parameters thereof can be "locked in", for example, by early regulatory filings. The inability to adequately investigate filtration parameters can jeopardize yields, purity, membrane durability, etc., in the resulting industrial scale process, potentially delaying and/or frustrating commercialization.

Traditional methods of TFF process development require tedious, repetitive methodologies that, when performed manually, consume considerable time, and effort. There is need thus for an automatic process development device that a developer can use to design and run TFF processes on a laboratory scale and, in the course thereof, automatically collect and/or process information needed for "scaling up" the subject processes for industrial-scale operation.

Certain research entities have already established large engineering departments that, when needed, can custom design automated process development systems. However, the costs associated with such undertaking is often considerable, and seemingly, only research entities with vast in-house resources and expertise can successfully develop such custom-built APDS systems. These systems, moreover, tend to be "application-specific", and consequently, have considerably limited commercial applicability.

Providing more flexible, more universal, and broader applicability in a single TFF process development device is problematic. Accommodating broad sample volume ranges, for example, is a particular concern, with both mechanical- and process-related issues being especially acute in the striking of an acceptable lower range (i.e., a minimum recirculation volume). Sample volumes in early process development stages—as is known—are often available only in minute quantities, and hence, cannot be squandered needlessly.

In light of the above—despite an existing need—there are currently no known automated TFF development devices capable of comprehensively acquiring meaningful developmental data, with a minimum sample volume requirement less than 20 ml.

SUMMARY

The present invention provides a fully-automated small-volume tangential flow filtration device capable of concentrating 0.5-5.0 liter batches of a sample liquid to less than 0.02 liters, and—in the course thereof—comprehensively acquiring and recording data useful for larger (industrial) scale development, qualification, and validation. The automated process is fast, economical, accurate, and repeatable.

The automated TFF process development device comprises a reservoir having a distinct multifunctional mixing zone, a tangential flow filtration module, an electronic data processing network for comprehensive developmental data acquisition, and a "fluid-economical" complement of pumps, valves, conduits, and sensors. The device components are selected and/or custom-engineered and assembled in an unprecedented combination affording, among other things, both fully automated operation and data acquisition, and with a comparatively low minimum recirculation volume. The device—owing to its "modularity"—can accommodate "traditional" TFF separation process development with (when desired) "HPTFF" and "HRTFF" process functionality.

In respect of the above, a principal object of the present invention is to provide an automated tangential flow filtration device for conducting TFF separation processes at a lab scale with minimal sample volume requirements, and for acquiring and recording data useful for larger scale development.

Another object of the present invention is to provide a stand-alone, fully-integrated, self-contained automated tangential flow filtration device for conducting separation processes with minimum sample volume requirements, and for acquiring and recording data thereabout.

Another object of the present invention is to provide an automated fluid filtration device useful for conducting fluid separations and acquiring process data thereabout, the device utilizing an innovatively constructed reservoir, having a continuous internal volume comprising a substantially cylindrical upstream enclosure which tapers (or otherwise commences decreasing in internal diameter) at a downstream end into a distinct mixing zone, said distinct mixing zone having a substantially fractionally smaller volume than the substantially cylindrical upstream enclosure, with a reservoir inlet and outlet, and a process stream sensor positioned or otherwise active in said distinct mixing zone.

Another object of the present invention is to provide an automated tangential flow filtration device having modular functional components, thereby facilitating disassembly, reassembly, and modular expansion.

Another object of the present invention is to provide a tangential flow filtration device incorporating an innovatively engineered reservoir that has, among other things, a low-volume multifunctional mixing zone, a vortex reducing sensor arrangement, and tight sanitary seal gaskets.

The following description considered in conjunction with the accompanying drawings will enable a further understanding of the nature of these and other objects of the invention.

BRIEF DESCRIPTION OF THE DRAWINGS

FIG. 1 illustrates a tank 111 used in an automated tangential flow filtration process development device 10 according to an embodiment of the present invention.

FIG. 2 illustrates in cross-section the tank 111 revealing further details of the construction of ultrasonic level sensor 168, tank base 102, distinct mixing zone 5, and jacket 180.

FIG. 3 illustrates another cross-section of the tank 111, orthogonal to the cross-section of FIG. 2, revealing further details of the construction of air jet port 106, and front and rear sight glasses 140.

FIG. 4 illustrates a top view of the tank 111, showing details of tank lid 104.

FIG. 5 illustrates a side view of tank 111, showing—among other things—the placement of inlet 130 in relation to distinct mixing zone 5.

FIG. 6 illustrates a bottom view of the tank 111,

FIG. 7 provides a schematic flow diagram of the automated tangential flow filtration process development device 10 according to an embodiment thereof. The embodiment includes optional functional modules. The optional functional modules, set off with dashed lines, includes: a "High-Resolution" Tangential Flow Filtration (HRTFF) Module 20, an Ultraviolet Absorbance Module 30, and a "High-Performance" Tangential Flow Filtration (HPTFF) Module 40.

FIG. 8 illustrates, in exploded view, a tangential flow filtration module 200 used in of the automated tangential flow filtration process development device 10 according to an embodiment of the present invention.

FIG. 9 illustrates an alternative tangential flow filtration module 200a, the module 200a being essentially a combination of single modules.

FIG. 10 illustrates an electronic data processing network 7 used in the automated tangential flow filtration process development device 10 according to an embodiment of the present invention.

FIG. 11 is a schematic representation of reservoir 100, showing the bounds of distinct mixing zone 5.

DETAILED DESCRIPTION

Figure 1:
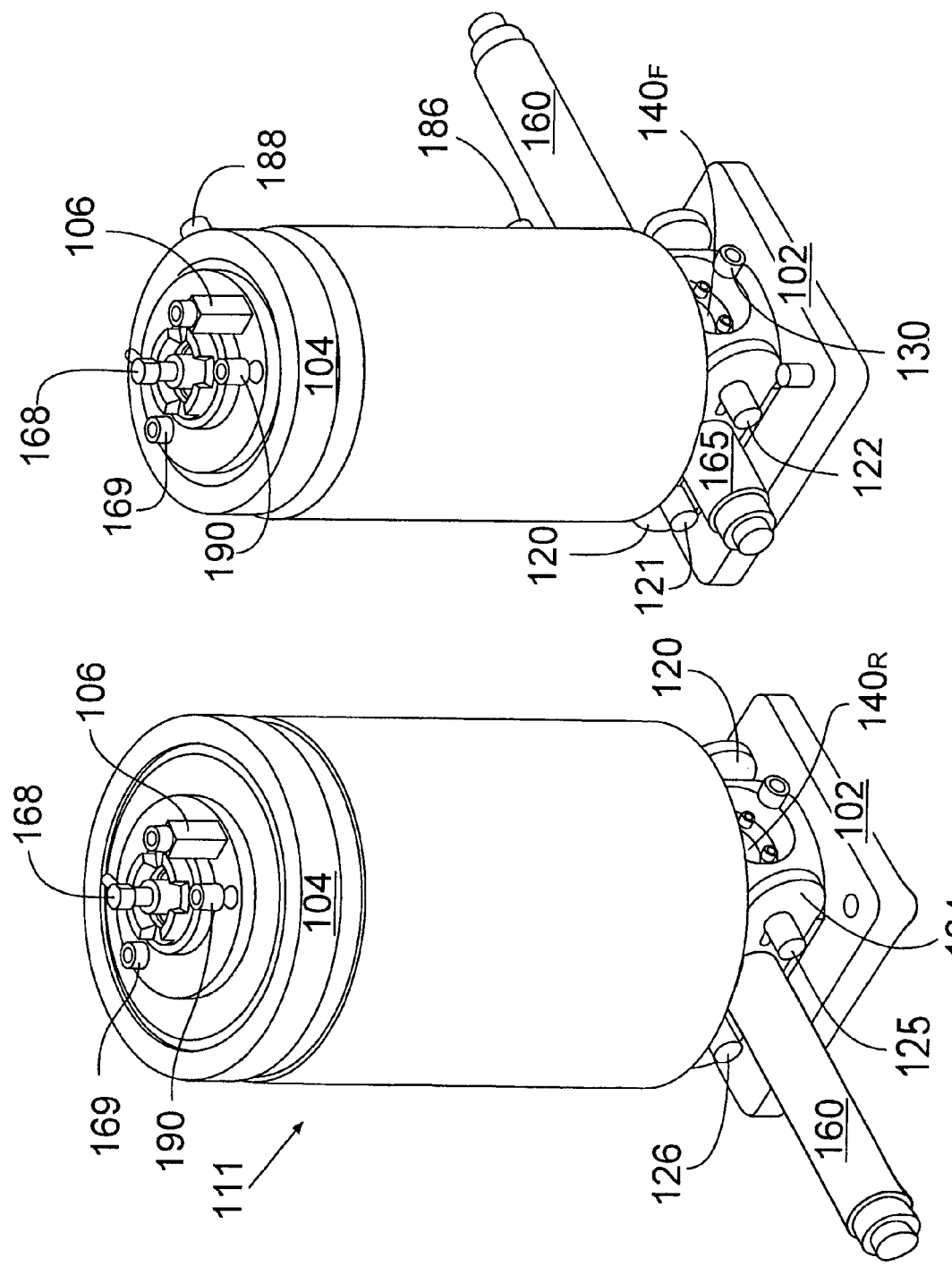
FIGS. 1 to 11 provide schematic representational illustrations. The relative locations, shapes, and sizes of certain objects are occasionally exaggerated to facilitate their description. Certain features—e.g., the wiring of electrical components in FIG. 7—are omitted for clarity.

The automated tangential flow filtration process development device 10 of the present invention—operable to an unprecedented minimum reliable recirculation volume of approximately 20 milliliters—comprises a reservoir having a distinct mixing zone; a tangential flow filtration module; a plurality of conduits defining, together with said distinct mixing zone and said tangential flow filtration module, a fluid process stream through which a liquid sample can be conducted; a plurality of pumps, valves, and sensors for driving, regulating, and acquiring data about said liquid sample as it flows through said fluid process stream; and an electronic data processing network capable of receiving, transmitting, processing, and recording data associated with the operation of said pumps, valves, and sensors.

The automated TFF process development device 10 enables automated process data acquisition at low fluid sample volumes. Toward such end, the process development device 10 is characterized by its unprecedented combination of several functionally-interrelated features. These features include, but are not limited to, the use of a distinct multifunctional mixing zone, the configuration of a recirculated fluid process stream having a minimum volume requirement no greater than 20 ml., and the integration of a dedicated electronic data process network.

The distinct mixing zone, located at a downstream end of the device's reservoir, is equipped with fluid sample sensor(s), enabling continued data acquisition within its substantially fractionally smaller volume. The positioning of the reservoir's inlets and outlets at said distinct mixing zone—together with appropriate selection and configuration of the device's conduits and TFF module—enables the accomplishment of said low minimum recirculation volume. Automation is enabled by the dedicated electronic data processing network, configured specifically to collect and record data associated with the operation of the device at a comprehensiveness sufficient to determine (e.g., by algorithmic extrapolation) the conduct of the investigated TFF process at a substantially larger scale.

The process development device is well-suited for developmental investigation of a broad range of TFF processes, involving lab-scale volumes of 0.5 to 2 liters. The investigation of biopharmaceutical filtration processes however is of particular interest in view of the amount of data and documentation typically required by regulatory agencies to "qualify" for commercial use said process. TFF-based biopharmaceutical processes include, for example, the concentration, diafiltration, and/or recovery of biomolecules; the harvesting and/or removal of cells; and the depyrogenation of biomolecule solutions.

All product contact surfaces of the device are desirably, made of FDA compliant and/or USP Class VI tested materials. The device and its components should also be compatible with all commonly used solvents for TFF, for example, 1N NaOh (at 50° C.), 400 ppm NaOCl (at 50° C.), 1.1% phosphoric acid, 1.8% acetic acid, 2M HCl, 2M urea, "Triton-X" (a non-ionic detergent produced by polymerization of octylphenol with ethylene oxide, available from the Union Carbide Company, Danbury, Conn.), "Tween" (a polysorbate), 30-50% hexalene glycol, 30-50% propylene glycol, 0.07% polysorbate 20, 0.01-0.02% polysorbate 80, 90% ethanol, 90% methanol, 90% isopropyl alcohol, and 25% acetonitrile (w/v water).

Preferred embodiments of the present invention (a) have a scalable concentration ratio matching the capability of larger systems and the ability to concentrate solutions to a final volume of 20 ml using 50 cm2 TFF XL devices; (b) have a pressure capability to 60 psi at 55° C.; (c) have a process temperature capability to 55° C.; (d) have a system accuracy to 2-3% of full range; (e) are validatable; and (f) are compliant with applicable public- and/or private-sector standards and/or regulatory requirements.

A key component of the automated tangential flow filtration process development device 10 is its innovative tank 111, characterized in certain respects by its distinct mixing zone and the provision therein of sample liquid sensor(s). A desirable configuration for tank 111 is shown in FIGS. 1 to 6. As shown, the reservoir 100 of tank 111 is substantially cylindrical in shape, rests on tank base 102, and is capped, at its open top, with multifunctional tank lid 104. A tight seal is effected innovatively at both interfaces utilizing sanitary seal gaskets, i.e., lid gasket 109 and base gasket 119. Base 102 provides a stable support for reservoir 100. It serves also as a manifold, and is provided accordingly with an integrally-formed reservoir outlet 132.

Multifunctional tank lid 104 is attachable to, and thereby closes, tank 111, by the provision of clamp 108. The clamp 108 is preferably of the collar clamp type, though others means of attachment (e.g., screws, clips, and the like) can be employed. Multifunctional tank lid 104 is provided with a number of functional components, i.e., air jet port 106, ultrasonic level sensor 168, ambient temperature sensor 169, and vent 190.

Figure 11:
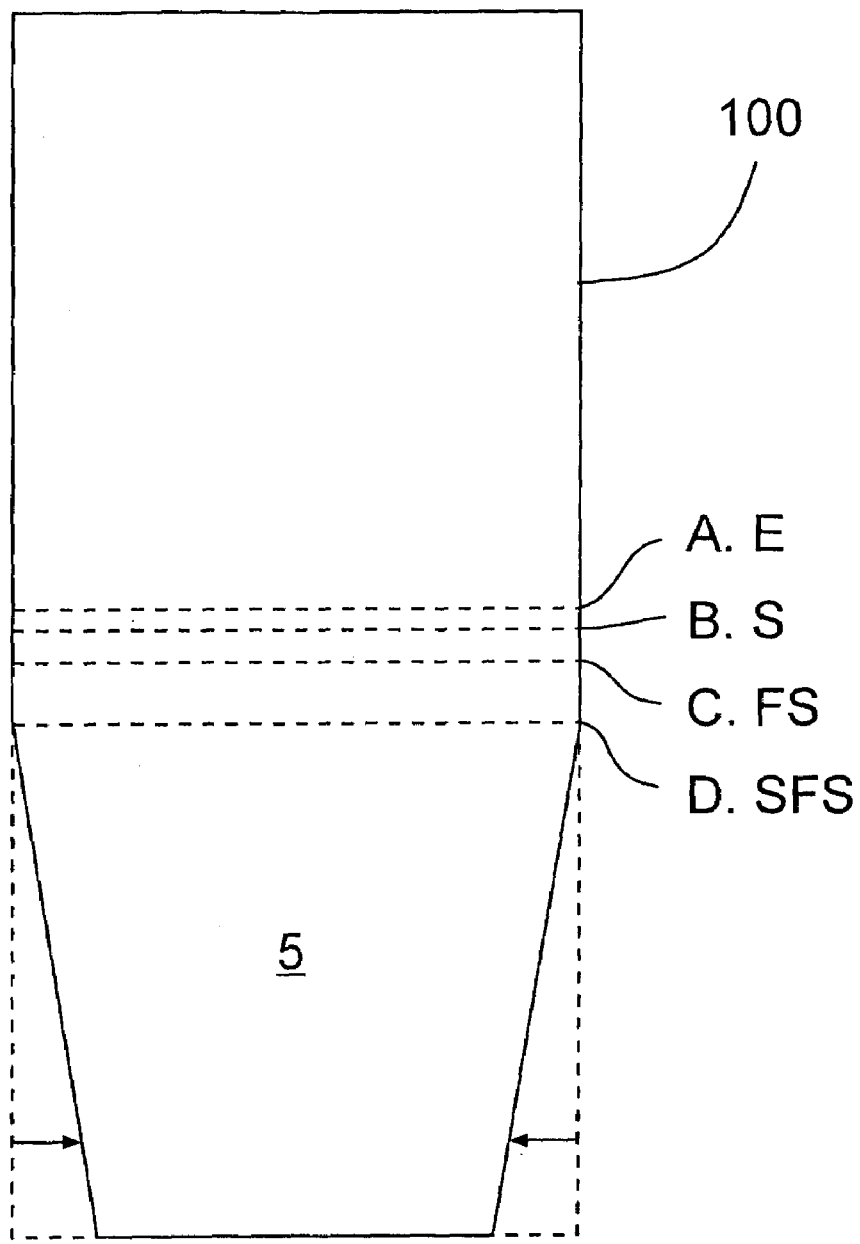

As shown in FIG. 11, the reservoir 100 of tank 111 has a continuous internal volume comprising an upstream substantially-cylindrical enclosure which tapers (or otherwise commences decreasing in internal diameter) at a downstream end into a distinct mixing zone 5. The mixing zone 5 has a substantially fractionally smaller "SFS" volume than the substantially-cylindrical enclosure and serves as the location where the reservoir inlet 130, the reservoir outlet 132, and at least one process stream sensor (e.g., 160 or 165) are positioned. For purposes of rough non-numerical quantification, the substantially fractionally smaller SFS volumes of the mixing zone 5 is compared in FIG. 11 to "equal", "smaller", and "fractionally smaller" volume levels "E," "S," "FS" within reservoir 100.

Provision of vent 190 in tank 111 enables control and maintenance of pressure in tank 111's internal reservoir 100. In one mode of operation (i.e., a so-called "blow down" procedure), vent 190 is closed to allow pressure to build up in the system 10 and thereby flush to waste excess liquid trapped within the system.

The other three components installed in tank lid 104 work together for the accurate determination of the liquid level in the tank 111's reservoir 100, central among which is an ultrasonic level sensor 168. By emitting ultrasonic signals and monitoring the reflected signal, sensor 168 can be used to determine fluid level. Ultrasonic level sensors are well known in the art. The preferred sensor is obtainable from Cosense Inc., 155 Ricefield Lane, Hauppauge, N.Y. 11788.

Since the propagation of sound is effected, among other things, by the temperature of the media through which it travels, an ambient temperature sensor 169 is installed in close proximity to the ultrasonic level sensor. Ambient temperature sensor 160 continuously acquires temperature readings, the data therefrom being sent to system 10's data processing network 7, whereupon, it can be factored together with the ultrasonic data for a more accurate determination of fluid level.

Figure 3:
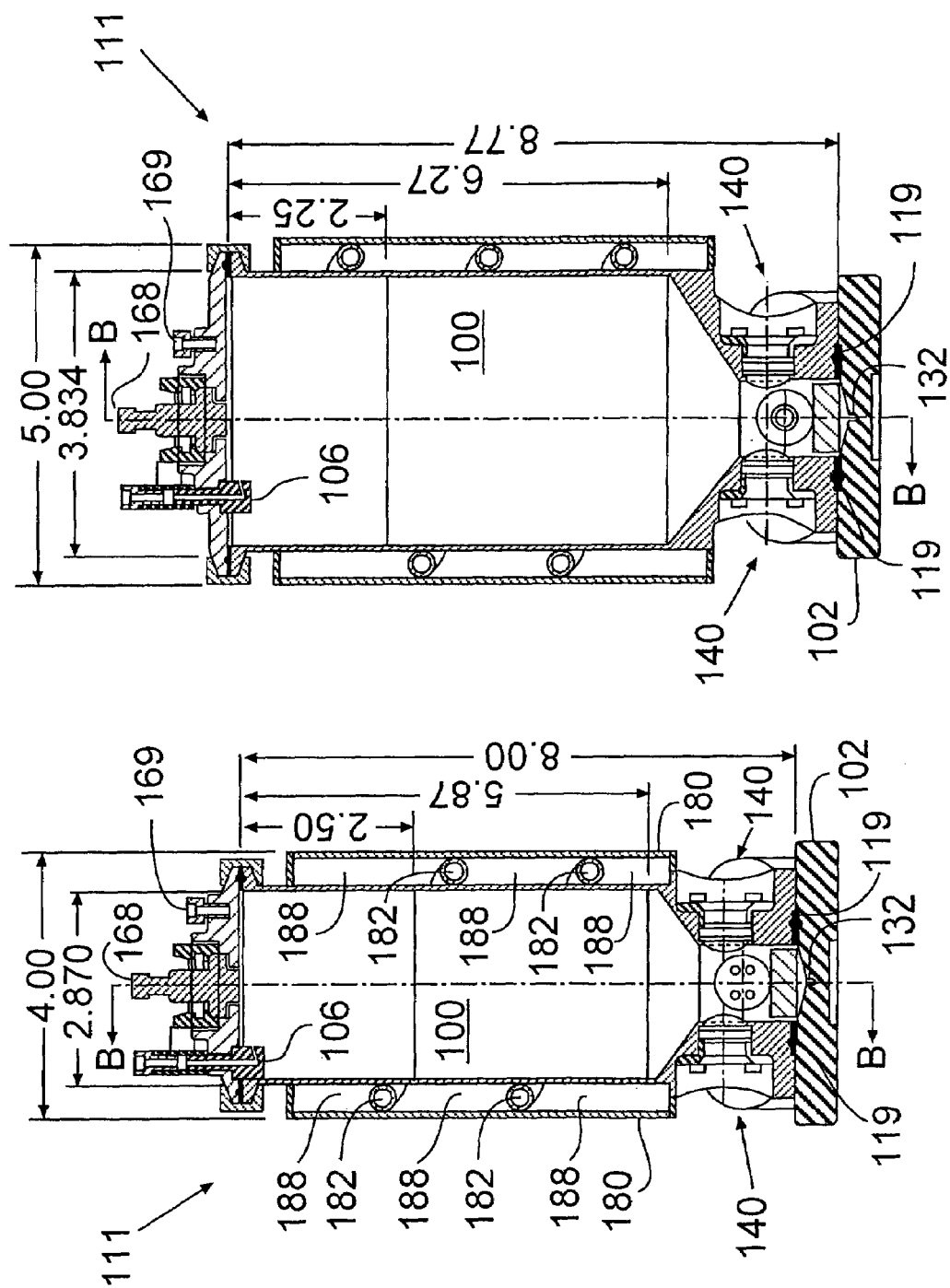
Figure 4:
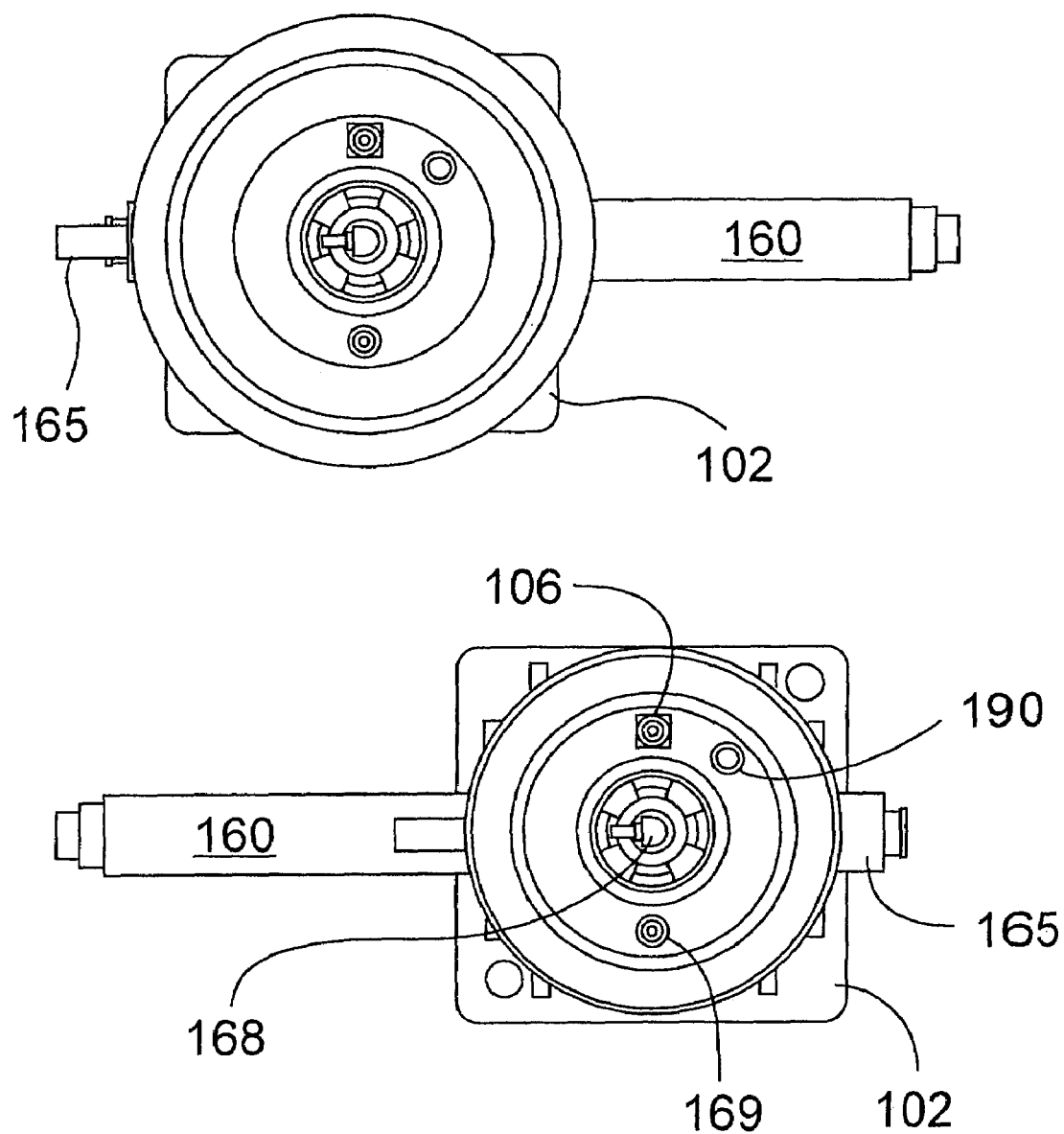
Figure 5:
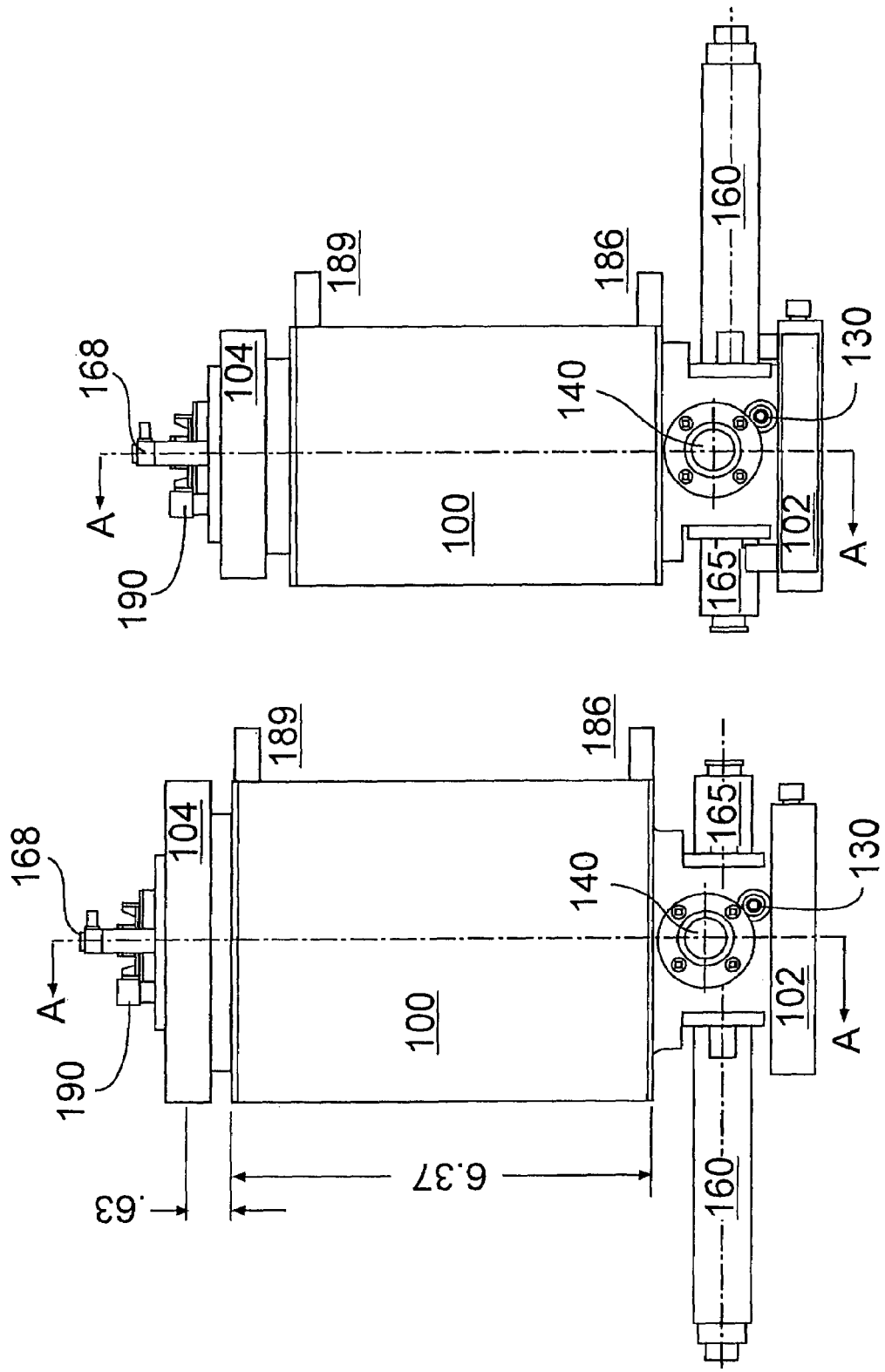
Figure 6:
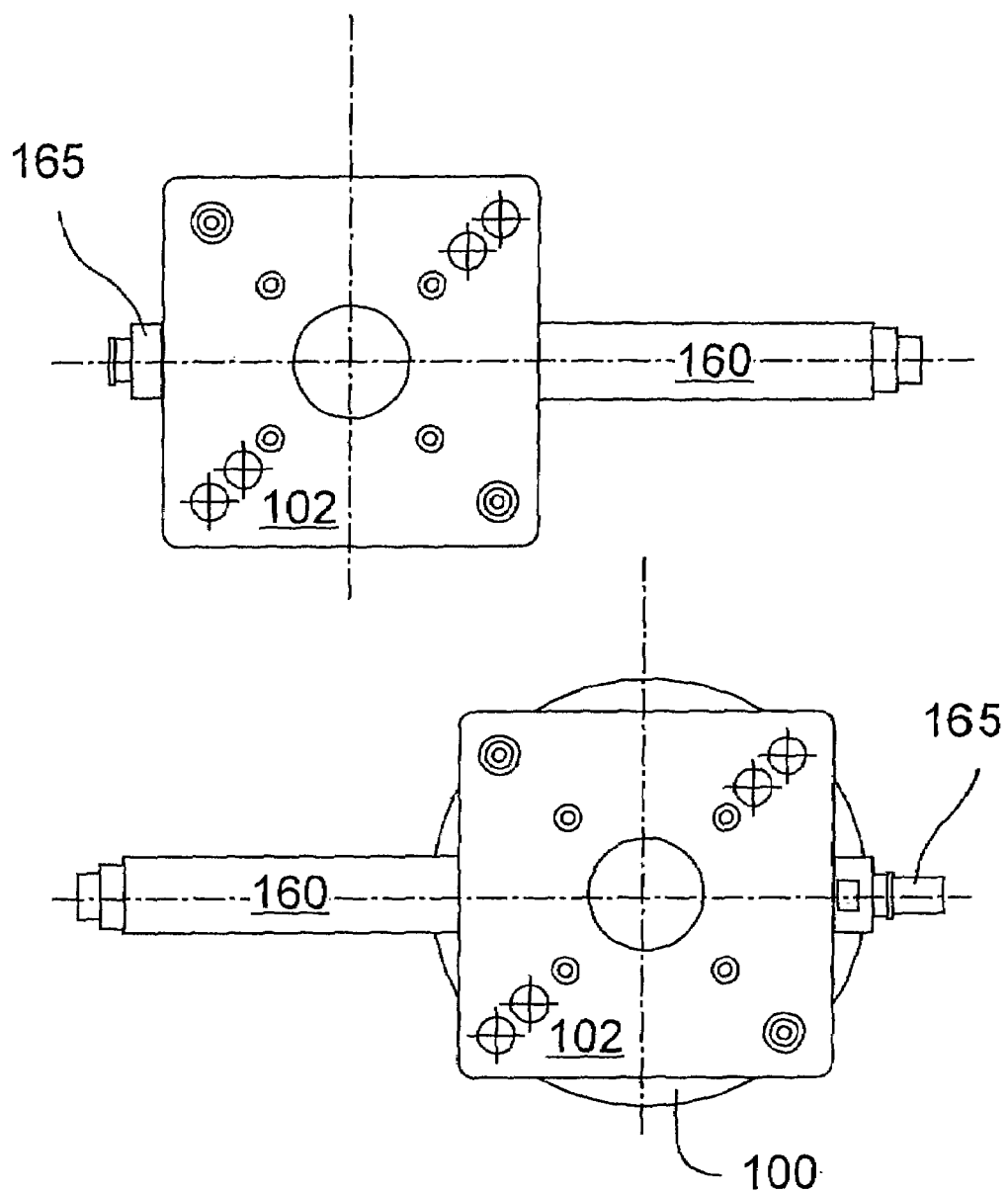

If vapor accumulates in reservoir 100, condensation can form on the ultrasonic level sensor 168, leading to spurious readings. To avoid this, an air jet port 106 is installed in close proximity to ultrasonic level sensor 168 as illustrated in FIG. 3. Air jet port 106 directs an air stream (i.e., through its nozzle) toward the face of sensor 168, removing and/or preventing condensation thereon.

Figure 2:
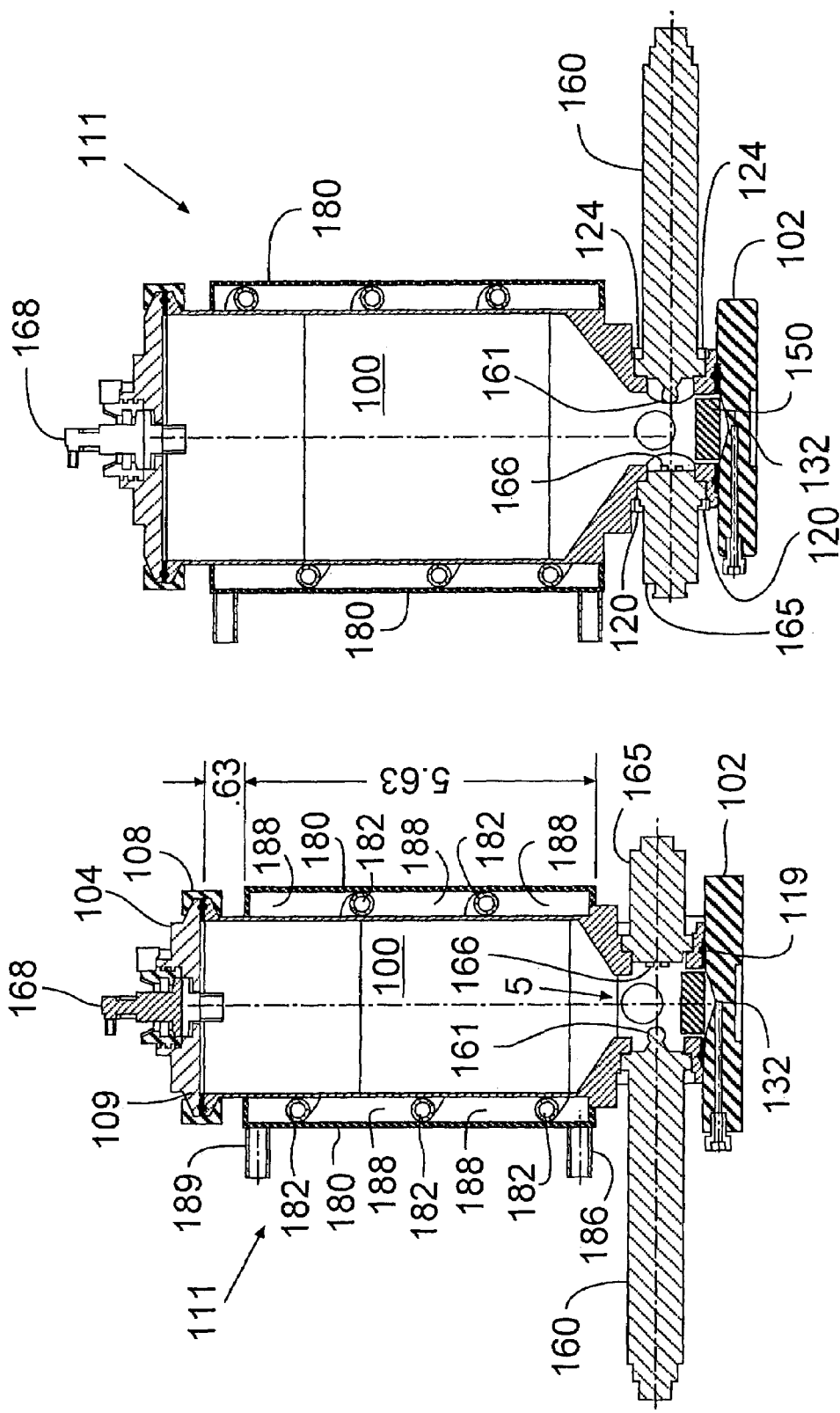

In accord with one aspect of the present invention, at least one of the sensors used to acquire, transmit, and record process information is positioned within the bottom area of the reservoir (see, mixing zone 5 in FIGS. 2 and 3). More preferably, two sensors (i.e., a pH sensor and conductivity sensor) are installed in this area. PH meter 160 is preferably a Wedgewood Model 1600-1200-00 meter, and temperature/conductivity meter 165 is preferably a Wedgewood Model BT-724 meter, both available from Wedgewood Technology, Inc., 3000 Industrial Way, San Carlos, Calif. 94070. The pH sensor 160 and temperature/conductivity sensor 165 are held in place relative to the reservoir 100 by sensor attachment plate 120 (using nuts 121 and 122) and sensor attachment plate 124 (using nuts 125 and 126

The particular installation of the reservoir sensor(s) is important to the accomplishment of low fluid recirculation volumes. As shown in FIGS. 1 to 6, the functionally-probing end of both sensors protrude into distinct mixing zone 5 of the reservoir 100, thus allowing the majority of sample fluid in the reservoir 100 to drain out, yet still leave adequate fluid for analysis and data acquisition.

Distinct mixing zone 5 can be provided with a magnetic stirrer 150, for mixing fluid, thereby yielding a more homogenous sample from which useful data can be acquired. The operation of a magnetic stirrer 150 in distinct mixing zone 5 can result in vortex formation, potentially frustrating the accomplishment of low recirculation volume By the protrusion of the functionally-probing ends of the sensors (i.e., bulb 161 of pH sensor 160 and probes 166 of temperature/conductivity sensor 165) into the mixing zone, physical obstacles are created that prevent, disrupt, or otherwise constrain vortex formation.

To visually inspect the internal operation of the mixing zone, tank 111 is provided with front and rear sight glasses 140$_F$ and 140$_R$. These are essentially portholes through tank 111, made of glass or other light transmissive material, through which an operator can visually inspect sample liquid. Its position at the bottom of tank 111 at the mixing zone 5 targets the area where more significant tank operations often occur, and where foreseeable system occurrences that can lead to failure (or other operational issue) may likely be localized. Thus, one can inspect for example the functionally-probing ends of both sensors, the operation of the magnetic stirrer, the condition and clarity of sample liquid, and the level of the sample liquid as it approaches a critical maximum drainage level. Though human visual inspection will be the most likely means for observation, the use of machine analysis is also possible. For example, one can use a photoelectronic device, such as a spectrophotometer, that can exploit to advantage the clear line of sight provided by the front and rear sight glasses 140$_F$ and 140$_R$, and in which case, attachment means and the use of optical elements may also be employed.

To maintain and control system temperature, tank 111 is provided with a jacket 180 surrounding reservoir 100. See FIG. 2. Jacket 180 defines an internal area 188 through which a fluid can flow from fluid inlet 186 and out of fluid outlet 189. In the embodiment shown in FIG. 2, jacket 180 does not cover the distinct mixing zone 5. To ensure that fluid flows completely around the reservoir, thus optimizing the contact area for heat exchange, a serpentine baffle 182 is coiled around the reservoir, ensuring that the cooling/heating fluid spirals around the exterior surface of the reservoir 100 before flowing out of the fluid outlet 189. The fluid can be gaseous or liquid, and can be either pre-heated or pre-cooled, and can be pressurized. Typical fluids are water, synthetic thermally-conductive liquids, oxygen, nitrogen, "freon", and the like. For biopharmaceutical investigation, water is currently preferred.

Preferably, the reservoir 100 will have a capacity of about 0.5 to 2.0 liters and will be equipped with both said cooling jacket and said magnetic stirrer and will be configured to allow complete drainage of sample liquid therefrom.

Preferably, magnetic stirrer's speed is set by the electronic data processing network 7 to a constant speed or adjusted in response to sample fluid level by an automatic control function thereof. The operating instructions for such automatic control is preferably established in consideration of the specific design features of the reservoir 100 to thereby help prevent or minimize vortex formation at low liquid levels.

Figure 7:
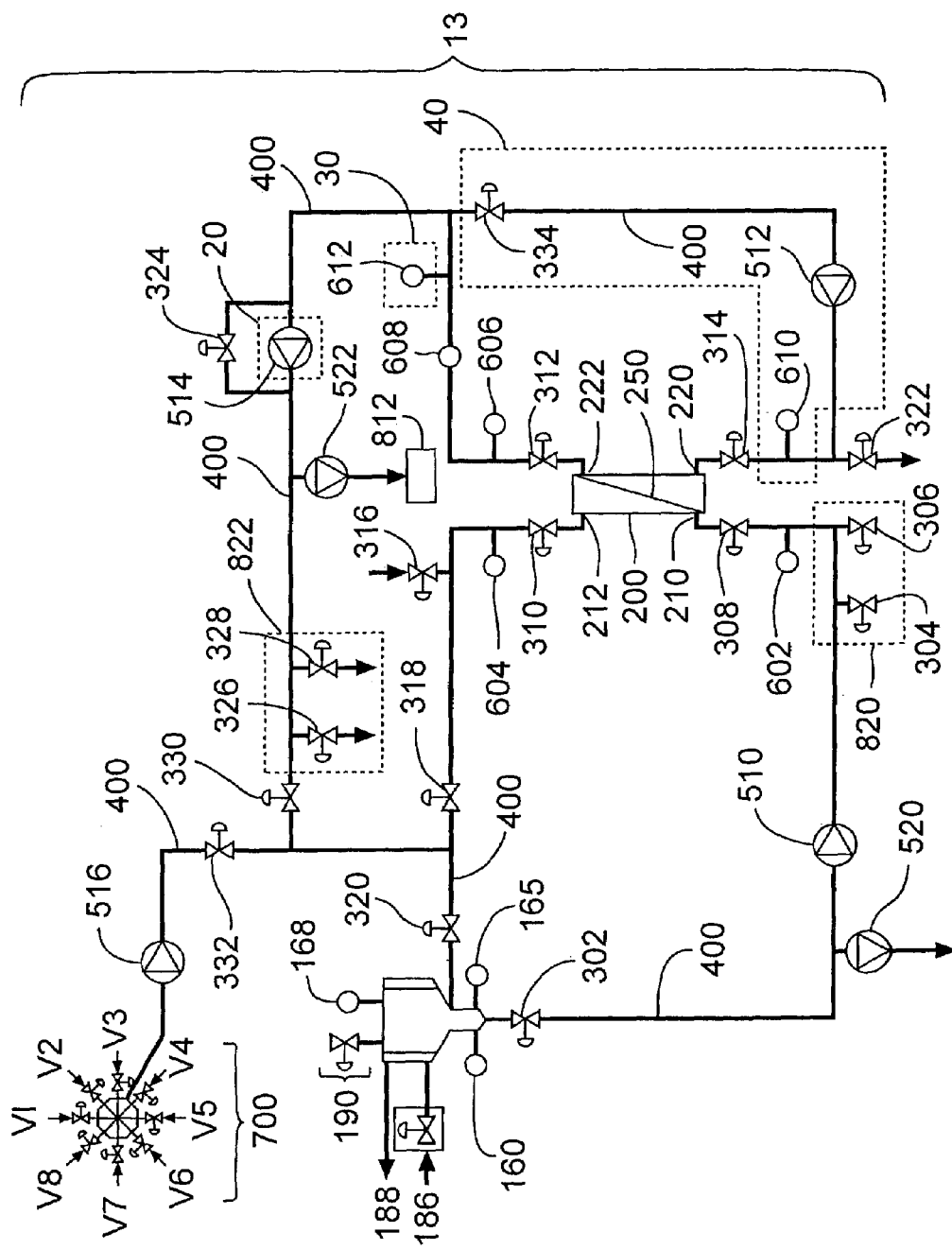

Although sample liquid is contained during operation in reservoir 100, in typical practice, the reservoir 100 is not the starting point or origin of said sample liquid. Rather, the typical source of fluid dispensed into system 10 is a multi-vessel liquid sample dispenser. An example of such dispenser is schematically illustrated in FIG. 7. As shown therein, a multi-vessel sample dispenser 700 is ultimately linked to reservoir 100. Multi-vessel sample dispenser 700 comprises multiple solution vessels V1-V8, each controlled by an electronically-controllable valve, and capable of being filled or otherwise loaded with varying solutions of fluid according to the process parameters of the particular separation application being pursued. Thus, for example, vessels V1-V8 can be filled with alternating solutions of deionized water, cleaning solution, buffer solution, and biochemical sample solution. The solutions are dispensed independently or in mixture under the electronic control of the system's data processing network 7 according to a preprogrammed regimen.

As shown in FIG. 7, the process development device 10 employs a tangential flow filtration module 200, comprising a feed inlet 210, retentate outlet 212, a permeate outlet 220, another permeate outlet 222, and a membrane 250. Suitable membranes include ultrafiltration, microporous, nanofiltration or reverse osmosis filters formed from polyvinylidene fluoride (PVDF), polysulfone, polyethersulfone, polyarylsulfone, regenerated cellulose, polyamide, polypropylene, polyethylene, polytetrafluoroethylene, cellulose acetate, polyacrylonitrile, vinyl copolymer, polyamides (such as "Nylon 6" or Nylon 66") polycarbonate, PFA, blends thereof or the like.

Other tangential flow filtration module configurations can be used, such as those that are well known in the art. Several types are described and/or disclosed in the patent literature: See e.g., U.S. Pat. No. 6,054,051, issued to R. D. van Reis on Apr. 25, 2000; U.S. Pat. No. 4,761,230, issued to J. F. Pacheco et al. on Aug. 2, 1988; U.S. Pat. No. 5,096,582, issued to A. A. Lombardi et al. on Mar. 17, 1992; U.S. Pat. No. 5,256,294, issued to R. D. van Reis on Oct. 26, 1993; and U.S. Pat. No. 5,525,144, issued to A. Z. Goilan on Jun. 11, 1996. They are also available commercially: E.g., "Pellicon XL" and "Pellicon 2" TFF cartridges (available from Millipore Corporation of Bedford, Mass. 01730); and "Centramate", "Centrasette", "Maximate" and "Maximate-Ext" TFF cartridges (available from Pall Corporation of East Hills, N.Y. 11548). For the present invention, the preferred tangential flow filtration modules are commercially-available lab-scale modules that belong to a "linearly-scaled" family (i.e., having linearly constant filtration parameter ratios throughout it member product range) and are engineered to minimize internal and "hold-up" volume, for example, the "Pellicon XL 50" of the Millipore "Pellicon" family of TFF cartridges.

Figure 8:
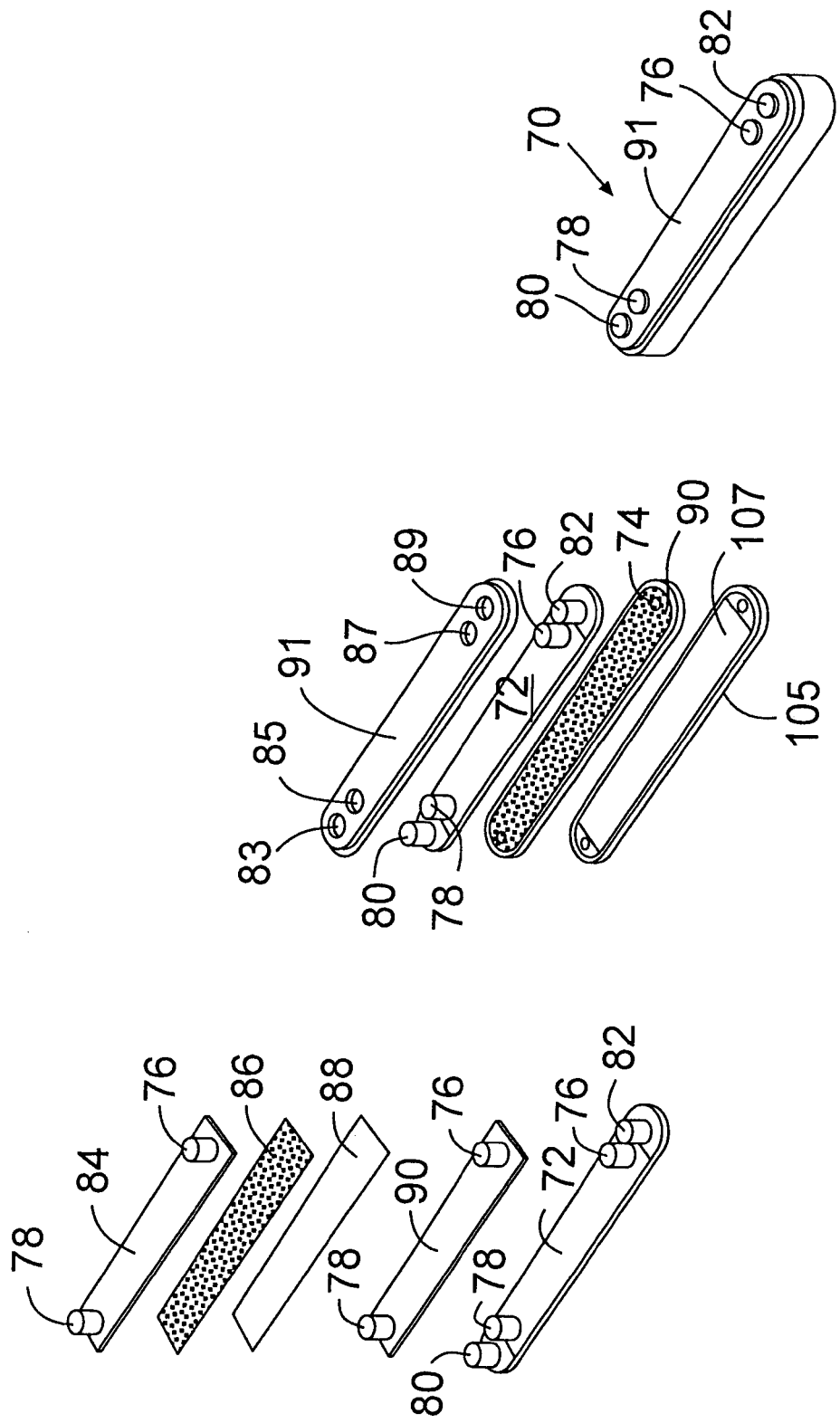

FIG. 8 illustrates one method for making a conventional tangential flow filtration module. The membrane filtration module 70 is formed from modules 72 and 107 and a feed spacer layer 74 and includes two permeate outlet ports 76 and 78, a feed inlet port 80, and a retentate outlet port 82. The module 72 is formed from an end cap 84, permeate screen 86, and a membrane 88. In the first step, the end cap 84, permeate screen 86 and membrane 88 are placed into a mold and are presealed to form a first overmolded element 90. The overmolded element 90 then is placed in a second mold and a plastic composition is molded about overmold element 90 to form second overmold element 72, including retentate outlet port 82, feed inlet port 80 and an end cap 91. End cap 91 has holes 83, 85, 87, and 89 to accommodate ports 76, 78, 80, and 82. The feed spacer 74 is formed by molding a rib 90 about the screen 74. Module 107 also is formed from an end cap 105, a permeate screen 86, and a membrane 83 in the same manner as module 72. Suitable seals are provided, such as with an adhesive, solvent bonding, ultrasonic welding, or the like to assure that permeate does not mix with feed or retentate while permitting formation of a permeate stream and a retentate stream. Suitable sealing compositions are structurally-compatible, low-degrading thermoplastic polymer composition including those based on polypropylene, polyethylene, PFA (perfluoroalkanes), PVDF, polysulfone, polyethersulfone, polyarylsulphone, polyamides, polycarbonate, acrylonitrile-butadiene-styrene (ABS), polyester, blends thereof, filled or unfilled, and the like.

Figure 9:
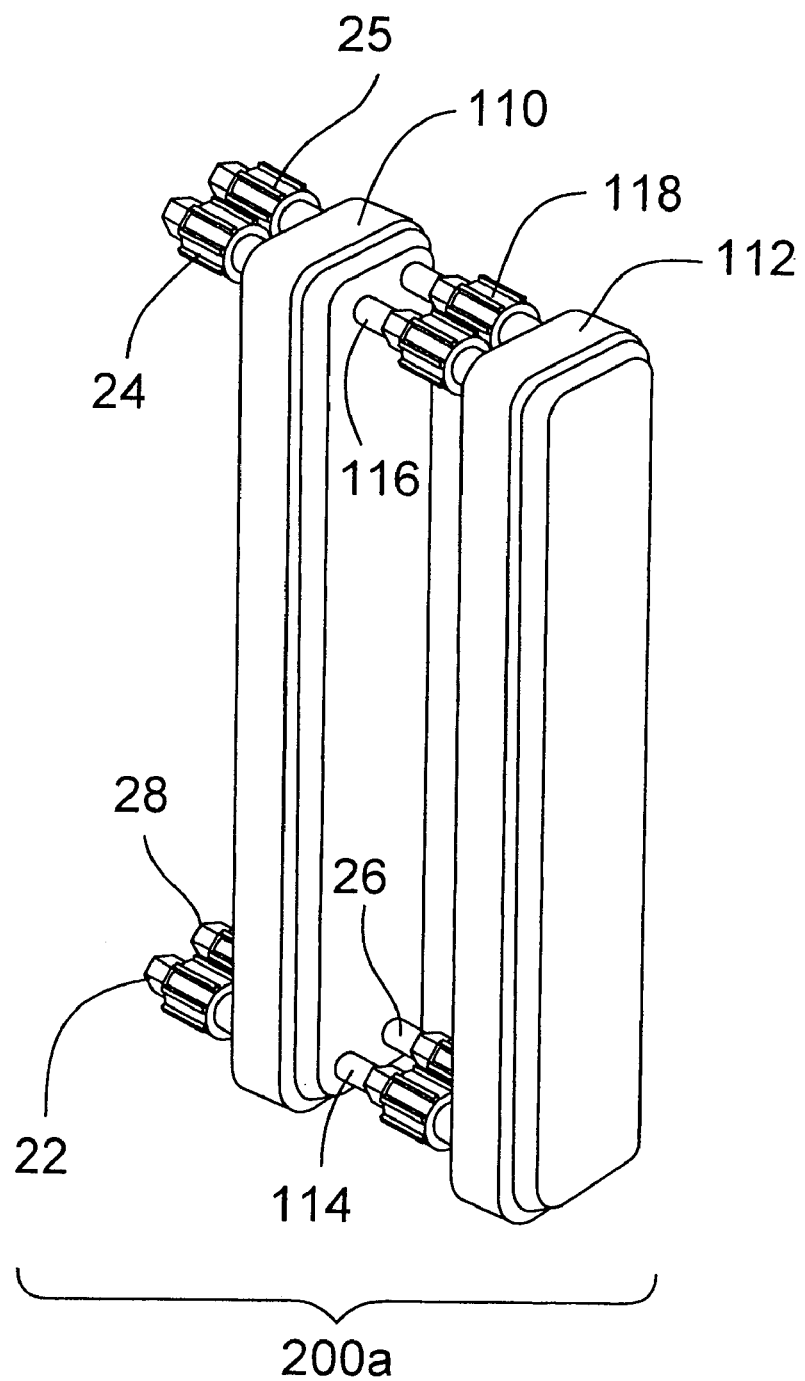

Referring to FIG. 9, two filtration modules 110 and 112 are shown connected to each other by feed connection 114, retentate connection 116, and permeate connection 118 and 26. Feed from the system 10 ultimately enters modules 110 and 112 through connections 22 and 114. Retentate is removed from the modules 110 and 112 through connections 116 and 24. Permeate is removed from the modules 110 and 112 through connections 26, 28, 118, and 25. The apparatus shown in FIG. 9 provides increased filtration capacity as compared to an apparatus utilizing a single filtration module.

The increased filtration capacity achieved through the use of two or more TFF modules can provide advantages which, for certain TFF applications, can offset the ensuing, concomitant, and otherwise unmitigated increase in the device's minimum recirculation volume—ie., an increase correspondent with the sum of the internal volumes of each additional module. To assist in the valuation of such increased filtration capacity, the following table provides filtration data for several multi-TFF module configurations.

| Pump | "A" Screen | | "C" Screen | | "V" Channel | |
|---|---|---|---|---|---|---|
| l/min | Devices | $m^2$ | Devices | $m^2$ | Devices | $M^2$ |
| 0.1 | 2 | 0.01 | 1 | 0.005 | 0 | 0 |
| 3.5 | 3 | 0.3 | 2 | 0.2 | 1 | 0.1 |
| 50-70 | 2 | 5 | 1 | 2.5 | 1 | 2 |
| 100-140 | 4 | 10 | 2 | 5 | 2 | 2 |
| 170-210 | 7 | 17.5 | 4 | 10 | 4 | 4 |
| 250-300 | 11 | 27.5 | 6 | 15 | 6 | 6 |
| 340-400 | 15 | 37.5 | 9 | 22.5 | 5 | 10 |
| 550-630 | 24 | 60 | 15 | 37.5 | 8 | 16 |
| 760-850 | 33 | 82.5 | 20 | 50 | 11 | 22 |

In the table, $m^2$ refers to the system's membrane area capacity based on pump capacity; an "A" Screen is a flow channel configuration suited for low viscosity and dilute applications; a "B" Screen is a flow channel configuration suited for low to intermediate viscosity applications; and a "C" Channel is a flow channel configuration suited for high viscosity and high product concentrations.

As shown in the automated tangential flow filtration process development device 10 of FIG. 7, a collection of conduits 400 are provided (or otherwise present) to establish passageways and avenues for the circulation and/or flow of sample liquid to or among the various system components and sub-modules. While the number, pattern, and complexity of the conduits will vary depending on the number of system components and sub-modules, in a basic embodiment of the inventive system, the conduits 400 should at the least define, together with the reservoir 100 (i.e., the distinct mixing zone 5 thereof) and the tangential flow filtration module 200, a fluid process stream through which the liquid sample is conducted, the process stream flowing from said reservoir 100, into said tangential flow filtration module 200, and back to said reservoir 100.

There is no particular limitations to the type of conduit used. Potential conduit types include, for example, rigid pipes, flexible tubing, and the channels and passages formed in or intrinsic to the device 10's other components (e.g., the device 10's valves and pumps). Typically, the plurality of conduits employed in the process development device 10 will include a mixture of conduit types. In a preferred embodiment, the bulk of the conduits employed are flexible, substantially biologically inert, synthetic polymeric tubing having an internal diameter of approximately 0.100 inches (0.254 cm).

Although sample liquid is intended to be circulated and re-circulated between the reservoir 100 and the tangential flow filtration module 200 during system operation, to withdraw samples and/or collect product from time to time as desired, the process development device 10 is configured as an "open" system. Along these lines, suitable mechanisms are incorporated to enable removal of sample fluid from the fluid process stream. The location and design of such mechanisms are not particularly critical. Regardless, for purposes of illustration, reference is made to FIG. 7, wherein pre-TFF sample collector 810 and post-TFF sample collector 812 are provided strategically before and after tangential flow filtration module 200 to allow removal of comparatively small volumes of sample liquid from the fluid process stream for later analysis and/or disposal.

In the embodiment represented in FIG. 7, collectors 810 and 812 are particularly configured together and in cooperation with the system 10's electronic data processing network, to allow a user to program for release specifiable (comparatively small) volumes of sample liquid. For withdrawal of larger volumes of sample liquid, the system 10 is provided with pre-TFF outlet 820 and post-TFF outlet 822. In contrast to the pre-and post-TFF sample collectors 810 and 812, the pre- and post-TFF outlets 820 and 822—though also under the device's electronic data processing network—are not "volume-specifiable".

A plurality of valves are positioned along or otherwise functionally proximate the fluid process stream for regulating the flow of liquid sample therethrough. In operation, flow of liquid through a valve will depend upon whether the valve is in an "open" or "closed" state or—in some circumstances—an intermediate state.

In the automated tangential flow filtration system 10 illustrated in FIG. 7, two types of electronically-controlled, in-line, solenoid valves are employed: i.e., (a) valves capable only of an "open" or a "closed" state (e.g., solenoid diaphragm valves available from NResearch, Inc. of West Caldwell, N.J. 07006), and (b) valves capable of a range of states between a fully "open" position and a fully "closed" position (e.g., proportionally-controllable solenoid valves, also available from NResearch, Inc.)

The "open-and-close" type valves have one primary regulatory function: i.e., they dictate whether and to what extent the fluid process will or will not be conducted further along downstream conduits. The proportional valves also have that function, but they additionally function to—as a consequence of their capacity to maintain intermediate "open" states—influence the pressure of the downstream and upstream pressure of the fluid process stream. This function is particularly relevant to the operation of valve 318, and specifically, its ability to accommodate transmembrane pressure differentials that often accompany usage of TFF-type membrane modules (e.g., TFF module 200).

Regardless of type, each valve—in respect of its placement, structure, and operation—should be considered with an eye toward minimizing, or more preferably, eliminating so-called "dead-space volume" in the process development device 10.

The following table sets forth the type (i.e., "proportional" or "open/close") and basic function of certain of the valves used in the system 10 illustrated in FIG. 7.

| Valve | Type | Function |
| --- | --- | --- |
| Valve 302 | Open/Close | Tank "shut-off" valve; Regulates passage of sample fluid out of reservoir 100 |
| Valve 304 | Open/Close | Pre-membrane sample recovery drain valve |
| Valve 306 | Open/Close | Pre-membrane sample waste drain valve |
| Valve 308 | Open/Close | Regulates passage of sample fluid (feed) into TFF module 200 through feed inlet port 210 |
| Valve 310 | Open/Close | Regulates passage of sample fluid (retentate) out of TFF module 200 through retentate outlet 212 |
| Valve 312 | Open/Close | Regulates passage of sample fluid (permeate) out of TFF module 200 through permeate outlet 222 |
| Valve 314 | Open/Close | Regulates passage of sample fluid (permeate) out of TFF module 200 through permeate outlet 220 |
| Valve 316 | Open/Close | Regulate so-called "blow-down" fluid for flushing device 10 |
| Valve 318 | Proportional | Used to regulate back pressure in TFF module 200 and thereby accommodate pressure differentials therein |
| Valve 320 | Open/Close | Regulates passage of sample fluid into reservoir 100. |
| Valve 322 | Open/Close | Filtrate drain valve |
| Valve 324 | Open/Close | Regulates bypass of sample fluid around HRTFF filtrate pump 314 |
| Valve 326 | Open/Close | Post-membrane sample waste drain valve |
| Valve 328 | Open/Close | Post-membrane sample recovery drain valve |
| Valve 330 | Open/Close | Filtrate recirculation valve |
| Valve 332 | Open/Close | Regulates the passage of sample fluid from liquid sample source 700 into the automated TFF device 10. |
| Valve 334 | Open/Close | Regulates passage of sample fluid into the co-flow HPTFF module 40 |

All valves identified in the above table are equipped with electric actuators for "on"/"off" analog control by the system 10's data processing network. With the exception of valve 318, all valves identified in the above table are "normally closed" in the device 10, i.e., they remain in a "closed" state unless activated by and thereby urged into an "open" state by device 10's data processing network. Other types of valves, such as pneumatically-operated valves, can be used.

As indicated, a plurality of pumps are positioned along or otherwise functionally proximate the device's fluid process stream to drive the flow of liquid sample therethrough. While pumps are preferred, other electronically-controllable means for driving sample liquid through the fluid process stream can be used.

In the automated TFF system illustrated in FIG. 7, essentially two types of "in-line" pumps are utilized, i.e., high-pressure positive displacement (HPPD) pumps and solenoid-activated diaphragm pumps. Other pump configurations—e.g., piezoelectric-driven, acoustically-driven, thermopneumatically-driven, electrostatically-driven, etc.—can be employed. Potentially useful fluidic micropump devices are disclosed, and/or suggested, and/or mentioned in, for example, U.S. Pat. No. 5,338,164, issued to R. F. Sutton et al. on Aug. 16, 1994; U.S. Pat. No. 4,938,742, issued to J. G. Smits on Jul. 3, 1990; U.S. Pat. No. 6,283,718, issued to A. Prosperetti et al. on Sep. 4, 2001; and U.S. Pat. No. 5,759,015, issued to H. Van Lintel on Jun. 2, 1998.

The solenoid-actuated diaphragm pumps (i.e., pumps 520 and 522) are a self priming, micro-dispensing, solenoid actuated micropumps, capable of providing a non-metallic, inert fluid path for the dispensing of high purity or aggressive fluids. Such pumps are available from Bio-Chem Valve, Inc. of Boonton, N.J. 07005.

The high-pressure positive displacement (HPPD) pumps operates such that the driven flow of liquid sample does not fluctuate unacceptably together with back pressure. In FIG. 7, the members of this class of pumps are HPPD Pump 510, HPPD Pump 512, HPPD pump 514, and HPPD Pump 516.

As indicated, a plurality of sensors are positioned along or otherwise functionally proximate the fluid process stream, each sensor capable of acquiring data about the liquid sample in their respective areas of sensitivity. The types of data desirably acquired are those pertaining to the tangential flow filtration process under investigation and relevant to the upward linear scaling thereof, and typically includes, but is not limited to, temperature, pH, pressure, concentration, flow rate, conductivity, flow rate and the like. Any detectors, probes, meters, and like sensing devices capable of acquiring such data can be utilized. Those skilled in the art will know of objectives for and methods of incorporating such sensing devices into the device. Incorporation will involve, among other things, establishment of connectivity with the data processing network 7.

A preferred collection of sensors is disclosed in the automated TFF device 10 illustrated in FIG. 7. In particular, aside from the sensors used in connection with the reservoir 100, the device 10's sensors include: a feed pressure sensor 602, a retentate pressure sensor 604, an upper filtrate pressure sensor 606, a filtrate flow meter 608, a lower filtrate pressure sensor 610, and a filtrate UV meter 612. The following table provides manufacturer and functional data for each sensor.

| Sensor | Manufacturer | Function |
| --- | --- | --- |
| Feed Pressure 602 | Foxboro ITC #19-100G-KOC | Sensor used for acquiring information regarding the pressure at the inlet of the feed channel of the TFF device. |
| Retentate Pressure Sensor 604 | Foxboro ITC #19-100G-KOC | Sensor used for acquiring information regarding the pressure at the outlet of the feed channel of the TFF device. |
| Upper Filtrate Pressure Sensor 604 | Foxboro ITC #19-100G-KOC | Sensor used for acquiring information regarding the pressure at the outlet of the filtrate channel of the TFF device. |
| Filtrate Flow Meter 608 | Badger Meter EMAC-40 | Meter used for acquiring information regarding the flow at the outlet of the filtrate channel. |
| Lower Filtrate Pressure 610 | Foxboro ITC #19-100G-KOC | An optional meter used for acquiring information regarding the lower filtrate pressure in the so-called "co-flow" loop, said information being important in HPTFF analyses. |
| Filtrate UV Meter 612 | Wedgewood AF44 | An optional meter used for acquiring information regarding the UV absorbance of molecules in the filtrate fluid. |

The preferred HPPD pumps are rotary reciprocating pumps such as disclosed in U.S. Pat. No, 5,863,187, issued to D. S. Bensley et al. on Jan. 26, 1999, and available from Ivek Corporation of North Springfield, Vt. 05150. In the interest of reducing the device's minimum recirculation volume, the HPPD pumps should be configured to eliminate or otherwise reduce the so-called "dead spaces" where fluid can collect.

For certain biopharmaceutical applications in which the sample liquid under investigation has substantial and significant protein content, forces and circumstances that can lead to the unintended and undesired denaturation of said proteins (i.e., the loss of the physical conformation of the protein's polypeptide constituency) should be avoided and/or mitigated. The mechanical shear forces often produced in the operation of certain pumps, particularly at gas/liquid interfaces (cf. e.g., bubbles), have been linked to protein denaturation, and accordingly, should be mitigated and/or avoided in the selection, manufacture, and incorporation of the device 10's pumps 510-522.

As indicated, the automated tangential flow filtration process development device 10 is provided with an electronic data processing network for receiving, processing, and recording data associated with the operation of, for example, the device's pumps, valves, and sensors, as well as from an external source (i.e., user input), and for transmitting signals (or other electronic instructions) to, for example, said pumps, valves, and sensors. The recorded data collected in the conduct of a tangential flow filtration process (at the device's "lab scale") should be sufficiently comprehensive to determine (e.g., by algorithmic extrapolation) the conduct of the tangential flow filtration process at a substantially larger scale. The data processing network will comprise circuitry, wiring, a user interface, data storage media, at least one CPU, and other electronic components, arranged to effect electronic connectivity and control of the device's components.

Figure 10:
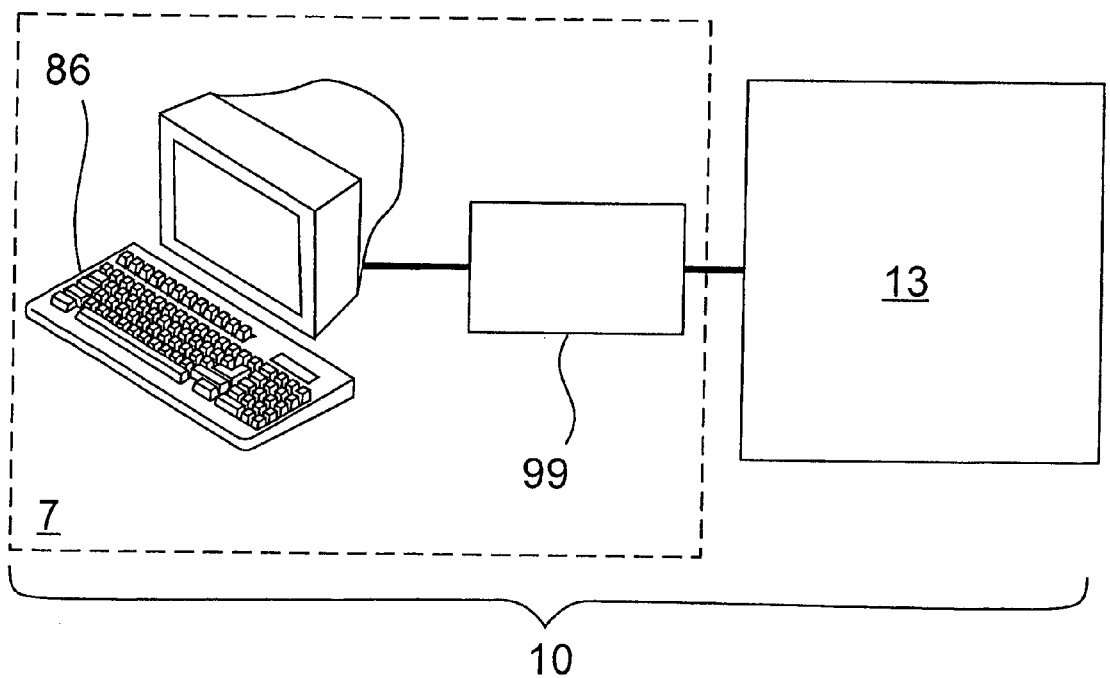

As shown in FIG. 10, the data processing network 7 can include a computer 86 linked to an industrial programmable logic controller (PLC) 99, the programmable logic controller 99 being itself linked to the electronically-controllable TFF hardware 13 (i.e., the system 10's pumps, valves, tank instrumentation, and sensors). The programmable logic controller is essentially a device-specific computer board or component capable of electronically receiving, processing, and transmitting electronic data. The programmable logic controller 99 operates with "raw" data and has embedded operating software therefor. Computer 86 communicates with, and to some extent controls, the programmable logic controller 99. Higher level operations can be assigned to computer 86. Computer 86 can be provided with input devices for acquiring external information (e.g., a keyboard) and output devices for external dispensation of information (e.g., a monitor, printers, network ports, removable magnetic or flash media drives, etc.).

Although it is preferred that computer 86 communicates indirectly with the TFF hardware 13 through the programmable logic controller 99, more direct communication is possible. Use of a programmable logic controller 99 afford advantage, however, in the easier replacement or substitution of computer 86, as well as enabling broader variability in its selection.

The presently preferred software used in computer 86 is described in commonly-assigned U.S. patent application Ser. No. 10/264,924, filed by L. Karmiy, B. Wolk, and C. Petersen on Oct. 4, 2002, entitled "Chemical Process Machine Programming System".

The computer 86 is preferably a "notebook"-type personal computer supplied with, among other things, a mouse (or other user interface). The notebook PC is connected to the PLC 99 with a standard RJ45 100Mbps Ethernet connection. The user (operator) interface for the device hardware is preferably on the front side of the device hardware at a user-convenient level. The power and e-communication plugs are preferably accessible from the side of the device hardware, for example, using a recessed box with a cover to maintain "Nema" rating. The device 10 is preferably configured to accept standard PC power cords for international connectivity provided that the Amp rating is sufficient. The system control software is preferably "user switchable" between bar and psi.

The electronic data processing network 7 preferably includes a "Common Control Platform" (CCP) (available from Millipore Corporation of Bedford, Mass.), the CCP being OPC compliant and capable of enabling the system to easily interface with other control platforms without customized programming. The CCP links all operations in the biopharmaceutical purification suite to a single automation, data acquisition, and batch reporting system. Using a single control system for all separation requirements significantly improves reliability and reduces the cost of operator training and system validation.

Preferably, a system display screen is provided to show the current process status, including valve positions, pump parameters, and the current active flow path All sensor information is shown in real time in both numeric and graphical formats. Changes to operating parameters and set point values are easily made by accessing an appropriate pull down menu. Process alarms, method status, and real time trends are displayed separately beneath the process synoptic Preferably, pump/motor speed performance elasticity should exceed a turndown ratio of 1 to 20. Retentate and permeate flow meters are fully functional with minimally conductive fluid. Level transmitted is accurate with WFI and with agitation in the tank.

Preferably, the system 10 is provided with a pump run time counter for maintenance purpose.

Preferably, information of differential pressure between feed and retentate ports on the TFF 200 module is used by the data processing network 7 to control the speed of the recirculation pump. This approach helps ensure that appropriate pressures are maintained during processing, with an automatic reduction of pump speed should viscosity increase during processing. Alternatively, the feed rate can be the controlled parameter.

Preferably, analog level control is provided to enable, in cooperation with the electronic data processing network, constant volume diafiltration for optimum use of dialysate and for high efficiency removal of small molecular species. The level control can also be used to allow processing of batches of sample liquid larger than the volume capacity of the device 10's reservoir 100. This can be accomplished by transferring feed from a larger auxiliary reservoir via a port on the selection valve.

Preferably, the device 10, in response to signals transmitted by the electronic data processing network 7, will sound an alarm (or otherwise provide notice to a system operator) when predetermined "high" limit alarm settings are exceeded. The electronic data processing network 7 can also be configured to shut down the device 10 when, for example, a "high-high" safety limit is exceeded; though, certain "high-high" safety limits may need to be protected from being disengaged, disabled, or otherwise circumvented in such manner. Alarms preferably remain active until acknowledged and a fault condition is rectified.

The automated tangential flow filtration device 10 can be characterized as a collection of modular functional blocks surrounding a core functional unit (i.e., the unit consisting only of those components immediately responsible for conducting the basic automated tangential flow filtration process). Ease of access to, substitution of, and replacement of each of the modular functional blocks leads to commercial and functional flexibility, and allows latitude for expansion by, for example, the addition of other (optional) functional modules. Certain of such optional functional modules are presented in FIG. 7 set off roughly by dashed lines, i.e., a "High-Resolution" Tangential Flow Filtration (HRTFF) Module 20, an Ultraviolet Absorption Module 30, and a "High-Performance" Tangential Flow Filtration (HPTFF) Module 40.

"High Resolution Tangential Flow Filtration" (HRTFF) is often employed to improve the separation of soluble proteins from, for example, suspended solids during clarification with microporous membranes and viruses during virus diafiltration with ultrafiltration modules. HRTFF typically employs a second pump (cf., pump 514) installed downstream from a permeate port to enable flux and transmembrane control. Without HRTFF functionality, certain separations can result in poor separation resolution as a result of, for example, membrane polarization (i.e., substances in the feed solution collecting on or near the surface of the membrane) or membrane fouling. A two-pump HRTFF system can prevent or mitigate such occurrence. In the present invention, the HRTFF module 20 comprises filtrate pump 514, and supporting conduits 400 and connectivity to the data processing network 7.

The Ultraviolet Absorption Module 30 is used for photometric analysis of the fluid process stream, and which is particularly useful in assessing protein concentration. In the present invention, the Ultraviolet Absorption Module 30 comprises ultraviolet sensor 612, and supporting conduits 400 and connectivity to the data processing network 7.

"High-Performance Tangential Flow Filtration" (HPTFF) is often employed to produce up to 1000 fold purification factors of protein mixtures containing similarly sized species. This is normally not possible in traditional size-exclusion based membrane processes. HPTFF technology exploits differences in the size and thickness of the ionic cloud surrounding proteins. This thickness can be manipulated by changing the pH and ionic strength of a sample solution. For example, albumin, which has a molecular weight of 64,000 kD can behave as a 300,000-400,000 kD molecule in the right buffer environment. Further details regarding HPTFF technology can be found, for example, in R. van Reis et al., Biotech, Bioeng., 56, 71-82, 1997; S. Saksena et al., Biotech. Bioeng., 43, 960-968, 1994; R van Reis et al., J. Membrane Sci., 129, 19-29, 1997; S. Nakao et al., Desalination, 70, 191-205, 1988; U.S. Pat. No. 5,256,294, issued to R. van Reis in 1993; and U.S. Pat. No. 5,490,937, issued to R. van Reis in 1996.

The automated tangential flow filtration system 10, by incorporating a so-called "co-flow" loop and control, automatically alters the central automated TFF conditions and operating parameters to allow performance of HPTFF purification techniques. The "co-flow" assemblage comprises "co-flow" pump 512, "co-flow" valve 334, lower filtrate pressure sensor 610, and supporting conduits 400 and connectivity to the data processing network 7. The "co-flow" loop and control provides the ability to maintain a constant transmembrane pressure (TMP) along the length of the TFF module 200. This is important for processing solutions for which molecular retention is affected by the TMP. In some cases, operation at a higher TMP can reduce the retentive capability of a membrane and yet in other cases increase the retention of small species for which the objective is to pass the membrane.

In addition to optional modules 20, 30, and 40, the automated tangential flow filtration system 10 includes a so-called "cartridge-blowdown" feature, enabling so-called "clean-in-place" (CIP) capability. Preferably, the system 10 is sanitizable using CIP procedures to reduce the level of bacterial contamination down to below 1 CFU/ml.

EXAMPLES

Example 1

An automated TFF process development device, electronically configured with the electronic data processing network described hereinabove, is structurally configured as set forth in FIG. 7 and the following Table:

| Parameter | Value |
| --- | --- |
| Membrane Area | 50 cm² |
| Minimum Recirculation Volume | <20 ml/PXL 50 |
| Concentration Ratio | <1 liter/m2 |
| Starting Volume | 200 ml to 1 L |
| Feed Pressure | 6 Bar (86 psi) |
| Feed Flow Rate | Up to 100 ml/min |
| Process Temperature | 4-55° C. |
| pH | 1-14 |
| Tanks | 1000 mL Recycle |
| Device Holder | PXL Standard |
| Pumps: | |
| Feed (range) | 0-100 ml/min at 80 psi |
| Filtrate (range) | 0-50 ml/min at 10 psi |
| Coflow (range) | 0-100 ml/min at 80 psi |
| Transfer (range) | 0-100 ml/min at 10 psi |
| Valves | On/Off |
|  | Retentate Back Pressure |
|  | 8 Port Selector |
| Pressure Indicators | |
| Feed | Range: 0-6 bar (90 psi) Accuracy: +/− 0.5% FS |
| Retentate | Range: 0-6 bar (90 psi) Accuracy: +/− 0.5% FS |
| Filtrate 1 | Range: 0-6 bar (90 psi) Accuracy: +/− 0.5% FS |
| Filtrate 2 | Range: 0-6 bar (90 psi) Accuracy: +/− 0.5% FS |
| Flow Indicators | |
| Feed w/Totalizer | Range: 0-100 ml/min Accuracy: +/− 1% FS |
| Filtrate w/Totalizer | Range: 0-60 ml/min Accuracy: +/− 1% FS |
| Transfer w/Totalizer | Range: 0-100 ml/min Accuracy: +/−1% FS |
| Temperature Indicator | Feed Range: 0-100° C.; Accuracy: +/− 1° C. |
| Control | Range: 4-50° C.; Accuracy +/− 1° C. |
| Level Indicator | Recycle Tank Range: 0-1000 ml. |
| Control | Range 0-1000 ml. |
| Mixing Agitator | Recycle Tank Range: 20-1000 ml |
| UV | Filtrate Permeate Line Range: 280 nm |

The automated TFF process development device provides consistent operation with good data acquisition using comparatively small sample volumes. As indicated in the table, the minimum recirculation volume is less than 20 ml.

While the present invention is discussed in reference to certain particular embodiments thereof, those skilled in the art, having the benefit of the teaching set forth herein can effect numerous modifications thereto. For example, modified embodiments can include, but are not limited to, the following an adapter manifold capable of operating, for example, a tangential flow filtration module comprising three "Pellicon XL"-type TFF cartridges, including collective permeate plumbing; a data processing network having an expanded batch recording feature that includes data fields for TFF cartridge lot number and release data (e.g., integrity and membrane water flux data); a data processing network wherein the means for receiving data from an external source is or includes a data reading device for reading machine readable data encoded on, for example, TFF cartridge labels and/or packaging, said data reading device including magnetic strip readers, bar code readers, optical scanners, and the like, said machine readable data including digitally encoded information recorded or printed on media, high and low density 2D and 3D bar codes, optical recordations, and the like; a data processing network capable of acquiring, recording, and processing information pertinent to system maintenance and calibration, said information including, for example, components requiring maintenance and calibration, servicing dates (historic and future), pump run time count information, and "clean-in-place" count information; a functional sub-module for conducting self-validation tests and, in the course thereof, generating OQ test documents, whereby comparative analysis of original factory-conducted validation tests results and subsequent user-conducted validation test results can yield information pertinent to the system's performance over time; and a disposable plumbing train. These and like modifications are to be construed as being encompassed within the scope of the present invention as set forth in the appended claims.

The invention claimed is:

1. An automated tangential flow filtration process development device for conducting a lab-scale tangential flow filtration process at a low minimum recirculation volume and acquiring process development data thereabout, the process development device comprising:
   (a) a reservoir suitable for containing a fluid sample and having a reservoir inlet and reservoir outlet, said reservoir having a continuous internal volume comprising a substantially cylindrical upstream enclosure which tapers at a downstream end into a distinct mixing zone, said distinct mixing zone having a substantially fractionally smaller volume than the substantially cylindrical upstream enclosure, said reservoir inlet and reservoir outlet being positioned in said distinct mixing zone;
   (b) a tangential flow filtration module having a feed inlet, a retentate outlet, a permeate outlet, and a membrane capable of separating the liquid sample into a retentate stream and a permeate stream upon passage of said liquid sample into the tangential flow filtration module through the feed inlet;
   (c) a plurality of conduits defining, together with said distinct mixing zone and said filtration module, a fluid process stream through which said fluid sample is conducted, wherein said fluid process stream flows from said distinct mixing zone, into said filtration module, and recirculated back to said distinct mixing zone, wherein the minimum recirculation volume of said fluid process stream is no greater than 20 milliliters;
   (d) a plurality of pumps and valves for driving and regulating the flow of said fluid sample through said fluid process stream;
   (e) a plurality of sensors for acquiring data about the fluid sample as it flows through said fluid process stream, a functional probing end of at least one of said plurality of sensors being positioned within said distinct mixing zone; and
   (f) an electronic data processing network capable at least of receiving, transmitting, processing, and recording data associated with the operation of said pumps, valves, and sensors and wherein the recorded data collected in the conduct of said tangential flow filtration process at said lab-scale is sufficiently comprehensive to determine the conduct of said tangential flow filtration process at a substantially larger scale.

2. The automated tangential flow filtration process development device of claim 1, wherein the functional probing end of said at least one sensor protrudes sufficiently into said distinct mixing zone to substantially disrupt vortex formation.

3. The automated tangential flow filtration process development device of claim 2, wherein functionally probing ends of two sensors are positioned within said distinct mixing zone, the first of said two sensors being a pH sensor, the second being a conductivity sensor.

4. The automated tangential flow filtration process development device of claim 1, further comprising one or more alternative process flow paths integrated into said fluid process stream, wherein fluid access into said alternative process flow paths is user selectable, and wherein said fluid process stream includes each user-selected alternative process flow path.

5. The automated tangential flow filtration process development device of claim 4, wherein said alternative process flow paths includes an HRTFF (high resolution tangential flow filtration) loop, said HRTFF loop comprising a user-activated second pump located in the permeate stream between the tangential flow filtration module and the reservoir; said HRTFF loop capable of effecting separation resolution when said second pump is activated.

6. The automated tangential flow filtration process development device of claim 4, wherein said alternative process flow paths includes an HPTFF (high performance tangential flow filtration) loop, said HPTFF loop capable when selected of effecting transmembrane pressure along the length of said membrane by provision of a co-flow pathway for said permeate stream, the permeate stream being re-circulated into said tangential flow filtration module by said co-flow pathway, the co-flow pathway of said HPTFF loop comprising at least a co-flow pump and a co-flow pressure sensor.

7. The automated tangential flow filtration process development device of claim 1, wherein said sensors includes an ultraviolet sensor integrated into the permeate stream of said fluid process stream.

* * * * *